United States Patent
Griffin et al.

(10) Patent No.: US 7,207,999 B2
(45) Date of Patent: Apr. 24, 2007

(54) SAFETY SCALPEL

(76) Inventors: Michael D. Griffin, 19761 Bahama St., Northridge, CA (US) 91324; Rodolfo Gaba, 722 Harper St., Simi Valley, CA (US) 93065

( * ) Notice: Subject to any disclaimer, the term of this patent is extended or adjusted under 35 U.S.C. 154(b) by 143 days.

(21) Appl. No.: 10/800,306

(22) Filed: Mar. 12, 2004

(65) Prior Publication Data

US 2005/0203555 A1    Sep. 15, 2005

(51) Int. Cl.
*A61B 17/32* (2006.01)
(52) U.S. Cl. .................................... 606/167
(58) Field of Classification Search ............... 606/167, 606/162, 163; 30/162, 156
See application file for complete search history.

(56) References Cited

U.S. PATENT DOCUMENTS

| | | | |
|---|---|---|---|
| 4,922,614 A * | 5/1990 | Machida | 30/339 |
| 5,078,724 A * | 1/1992 | Takase | 606/167 |
| 5,139,507 A | 8/1992 | Dolgin et al. | 606/167 |
| 5,207,696 A | 5/1993 | Matwijcow | 606/167 |
| 5,324,299 A * | 6/1994 | Davison et al. | 606/167 |
| 5,342,379 A | 8/1994 | Volinsky | 606/167 |
| 5,527,329 A | 6/1996 | Gharibian | 606/167 |
| 5,599,351 A | 2/1997 | Haber et al. | 606/167 |
| 5,676,677 A | 10/1997 | Landis et al. | 606/167 |
| 5,792,162 A | 8/1998 | Jolly et al. | 606/167 |
| 5,830,226 A | 11/1998 | Webb et al. | 606/167 |
| 5,868,771 A * | 2/1999 | Herbert et al. | 606/167 |
| 5,938,675 A | 8/1999 | Gharibian | 606/167 |
| 5,938,676 A | 8/1999 | Cohn et al. | 606/167 |
| 5,941,892 A | 8/1999 | Cohn et al. | 606/167 |
| 6,053,929 A | 4/2000 | Cohn et al. | 606/167 |
| D473,649 S | 4/2003 | Howell et al. | D24/147 |
| 6,626,925 B2 | 9/2003 | Newman et al. | 606/167 |
| 6,629,985 B1 * | 10/2003 | Kiehne | 606/167 |
| 2002/0143352 A1 * | 10/2002 | Newman et al. | 606/167 |

* cited by examiner

*Primary Examiner*—Michael J. Hayes
*Assistant Examiner*—M. Thomas Andersen
(74) *Attorney, Agent, or Firm*—Cislo & Thomas LLP (57) ABSTRACT

Presented herein are various embodiments of a safety scalpel. According to one embodiment is a safety scalpel system including handle capable of coupling to a blade with or without a safety housing.

28 Claims, 5 Drawing Sheets

SAFETY SCALPEL

BACKGROUND

Surgical scalpels may have a sturdy handle and a blade portion removably mounted on the handle for use during a given procedure. After the blade has been used, the blade may be removed and discarded, after which the handle may be sterilized and made ready for further use by mounting a new blade. New blades may be packaged in individual sterile packages formed by two sheets of paper or aluminum foil sealing the blade between them, much like finger bandages are packed.

When the blade is to be mounted on the handle, one paper or aluminum foil layer is folded back to expose the rearward or mounting portion of the blade. The package is then grasped so as to press the sides of the blade between the thumb and forefinger while the handle is inserted into the opening of the blade. While the blade should be held so that the cutting edge points away from the user, the potential for injury still exists.

Slipping of the blade within the paper or aluminum foil, in conjunction with the force required to properly install the blade on the handle, may push the blade through the cover and cause injury. Nothing prevents the blade from moving relative to its envelope and nothing prevents the blade from puncturing the cover. Therefore, individuals are subject to injury while installing the blade on the handle.

Upon completion of the surgical procedure, the blade may be either manually detached from the handle and placed in a sharps bin, or the handle with the blade may be inserted into a container, which may break off the blade.

It can be seen that attachment of the blade to the handle may be a hazardous procedure and can easily result in a sharps injury. If the blade is manually detached, a sharps injury can also result, which may be even more hazardous as the blade may be contaminated.

During surgical use, the scalpels can accidentally cut the surgeon's fingers, or the fingers of nurses and other support personnel. Furthermore, operating personnel may be accidentally cut when the scalpel is passed between personnel. Blades may need to be quickly removed from the handle during surgery. This may increase the likelihood of injury to either the surgeon or others.

Surgeons may have a personal preference as to a particular scalpel handle. The surgeon may prefer a certain weight and feel of a handle for achieving desired results in surgery. Furthermore, some safety systems allow for only a certain handle and certain blade systems to be utilized together.

What is needed is a safety scalpel system that would allow for specifically weighted, reusable handles to be used with safety and/or normal scalpel blades.

SUMMARY

Presented herein are various embodiments of a safety scalpel. In one embodiment is a safety scalpel includes a handle capable of coupling to a blade with or without a safety housing.

In another embodiment, a safety scalpel includes a blade, a handle configured to couple to the blade, and a housing configured to couple to, and enclose the blade, and to couple to the handle, and allow the blade to selectively couple to the handle and to selectively decouple from the housing, wherein the handle is configured to couple to the blade with or without the housing.

In yet another embodiment, a cartridge system includes retaining members configured to contain a blade within the housing, an actuatable tab or activator, wherein the blade couples to the handle and the housing moves between a safety position and a blade exposed position, and a blade disengaging actuator configured to decouple the blade contained within the housing from the handle.

DETAILED DESCRIPTION

The detailed description set forth below in connection with the appended drawings is intended as a description of exemplary embodiments and is not intended to represent the only forms in which the embodiments may be constructed and/or utilized. The description sets forth the functions and the sequence of steps for constructing and operating the illustrated embodiments. However, it is to be understood that the same or equivalent functions and sequences may be accomplished by different embodiments that are also intended to be encompassed within the spirit and scope of this disclosure.

Figure 1:
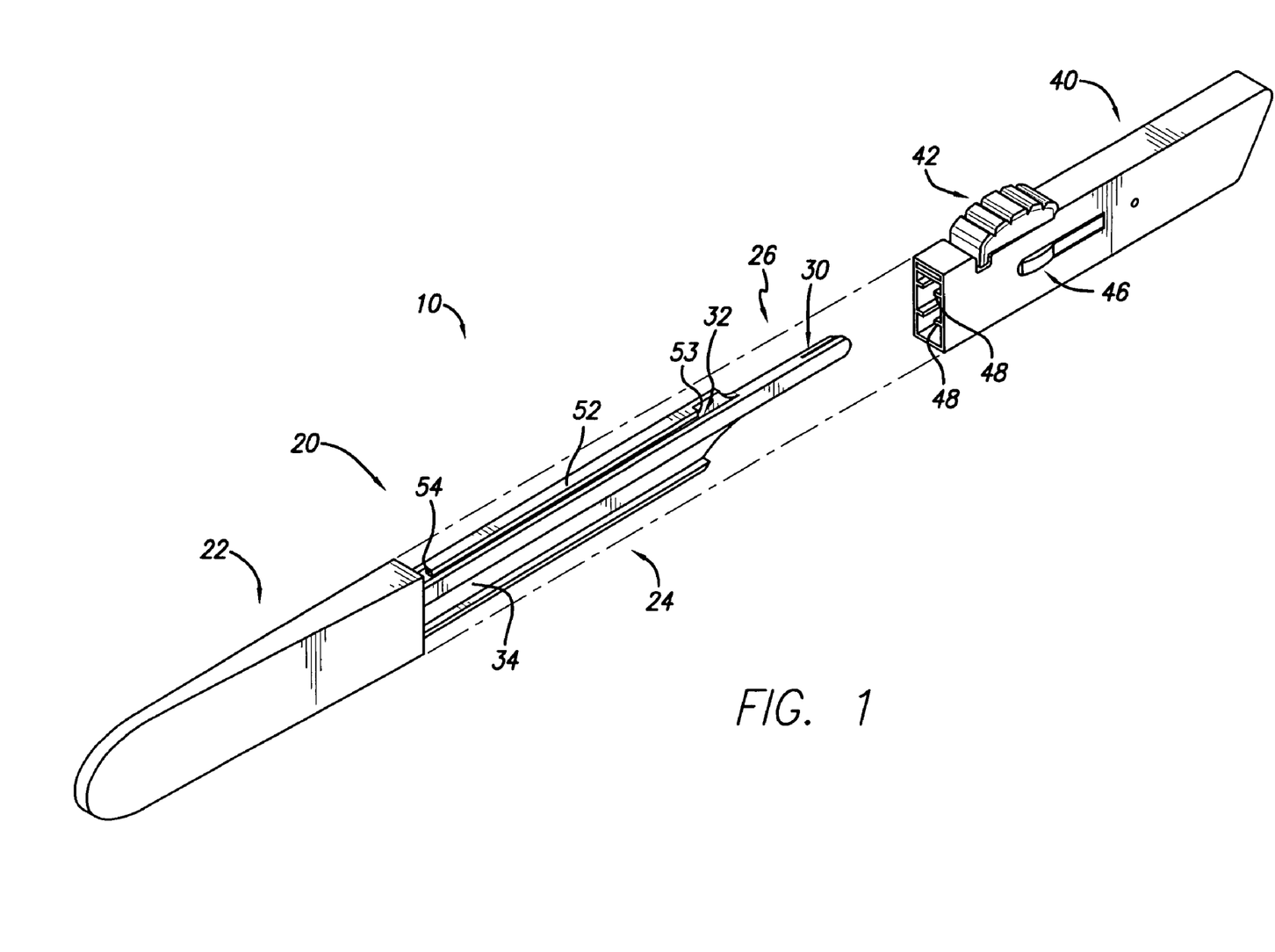
FIG. 1 is a perspective view of a safety scalpel system, according to an exemplary embodiment.

A safety scalpel system according to an exemplary embodiment is shown in FIG. 1, generally at 10. System 10 may include a handle 20 and a housing (cartridge) 40. The housing 40 is configured to house a blade and to couple to handle 20 such that the blade may couple to the handle and housing 40 may slide up handle 20 to expose the blade for use.

Handle 20 may include a grasping structure 22, which may be configured to be utilized by a user to hold the system when in use. Handle 20 may also include a housing receiving portion 24, which may be adjacent to, and coupled to, grasping structure 22. Furthermore, handle 20 may include a blade receiving portion 26 which may be adjacent to housing receiving portion 24. Blade receiving portion 26 may be configured to couple to a blade with or without housing 40. In this manner, the handle may be utilized with a bare scalpel blade, or it may be utilized with a blade within housing 40.

Handle 20 may be tapered, as shown or may have different configurations, including a uniform thickness, as desired by the preferences of the user. Furthermore, it may have other configurations to make it more comfortable to use and may be configured differently for each individual user.

Figures 3, 4:
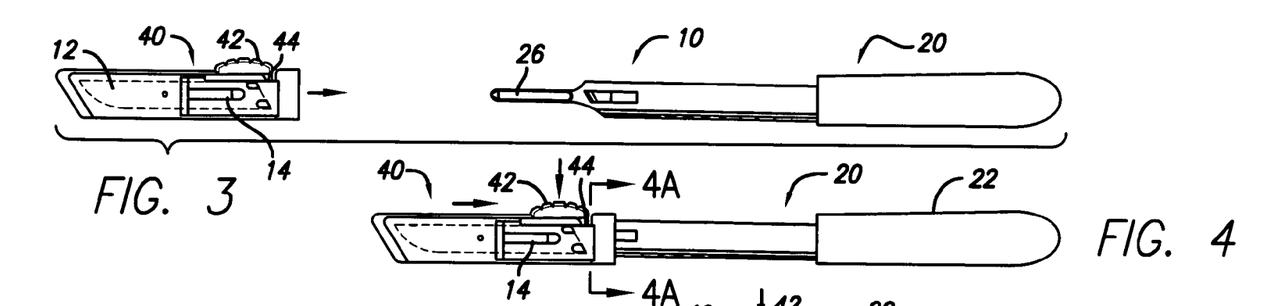
FIG. 3 is an elevational view of a safety scalpel system, showing the blade housing and a handle, according to an exemplary embodiment.
FIG. 4 is an elevational view of a safety scalpel system, showing the blade housing in a safe position, according to an exemplary embodiment.

Housing 40 may be configured to slide onto handle 20 in a safe position as the blade 12 may couple to blade receiving portion 26 while the housing 40 encloses the blade 12, as shown in FIG. 4. Blade receiving portion 26 may have a groove 30 that may be configured to fit into an orifice of a blade 12, and secure to the blade 12 such that a user may utilize the handle 20 and blade 12 as a scalpel. Housing receiving portion 24 may include a top channel 32 and a bottom channel 34 that may be configured to couple to, and receive portions of housing 40. This configuration may make the system more stable, as well as provide structure for coupling the housing 40 to the handle 20.

Figures 4A, 5, 6, 7, 8, 9:
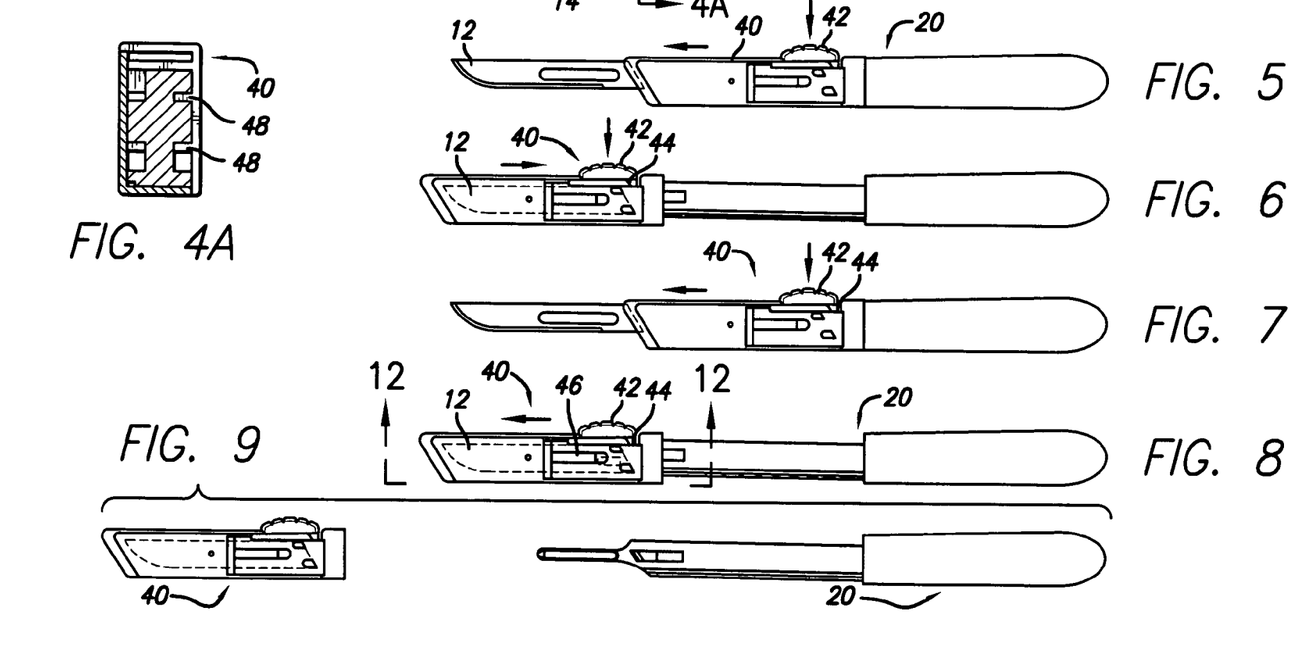
FIG. 4A is a cross-section view of the blade housing along line 4A—4A from FIG. 4, according to an exemplary embodiment.
FIG. 5 is an elevational view of a safety scalpel system, showing the blade housing in an exposed position with respect to a handle, according to an exemplary embodiment.
FIG. 6 is an elevational view of a safety scalpel system, showing the blade housing engaging a handle, according to an exemplary embodiment.
FIG. 7 is an elevational view of a safety scalpel system, showing the blade housing engaging a handle, according to an exemplary embodiment.
FIG. 8 is an elevational view of a safety scalpel system, showing the blade housing disengaging a handle, according to an exemplary embodiment.
FIG. 9 is an elevational view of a safety scalpel system, showing the blade housing apart from a handle, according to an exemplary embodiment.

Housing 40 may include a sliding movement tab or activator 42 and a blade disengaging actuator 46. Activator 42 includes a guide stop member 44 that will lock at opposite ends 53 and 54 of locking bar 52 (FIG. 1) to safely retain housing 40 at corresponding safety (blade covered) and "ready to use" (blade exposed) positions, as shown in FIGS. 4–5, respectively. Stop member 44 may be unlocked by pressing activator 42 in a generally downward direction, i.e. toward locking bar 52, as shown by respective directional arrows in FIGS. 4–7. The blade exposed position may be defined by housing 40 being coupled to housing receiving portion 24 and blade 12 being coupled to blade receiving portion 26 and exposed for use.

Tab 42 may be located on the top of housing 40, but may be located in other locations about housing 40 depending on the configuration, as desired. It will be appreciated that other means for allowing housing 40 to move may be utilized, as desired.

Housing 40 may also include stabilizing members 48 which may be configured to couple to top channel 32 and bottom channel 34 to ensure a proper coupling of housing 40 to handle 20, and to stabilize the entire system for use.

Figure 2:
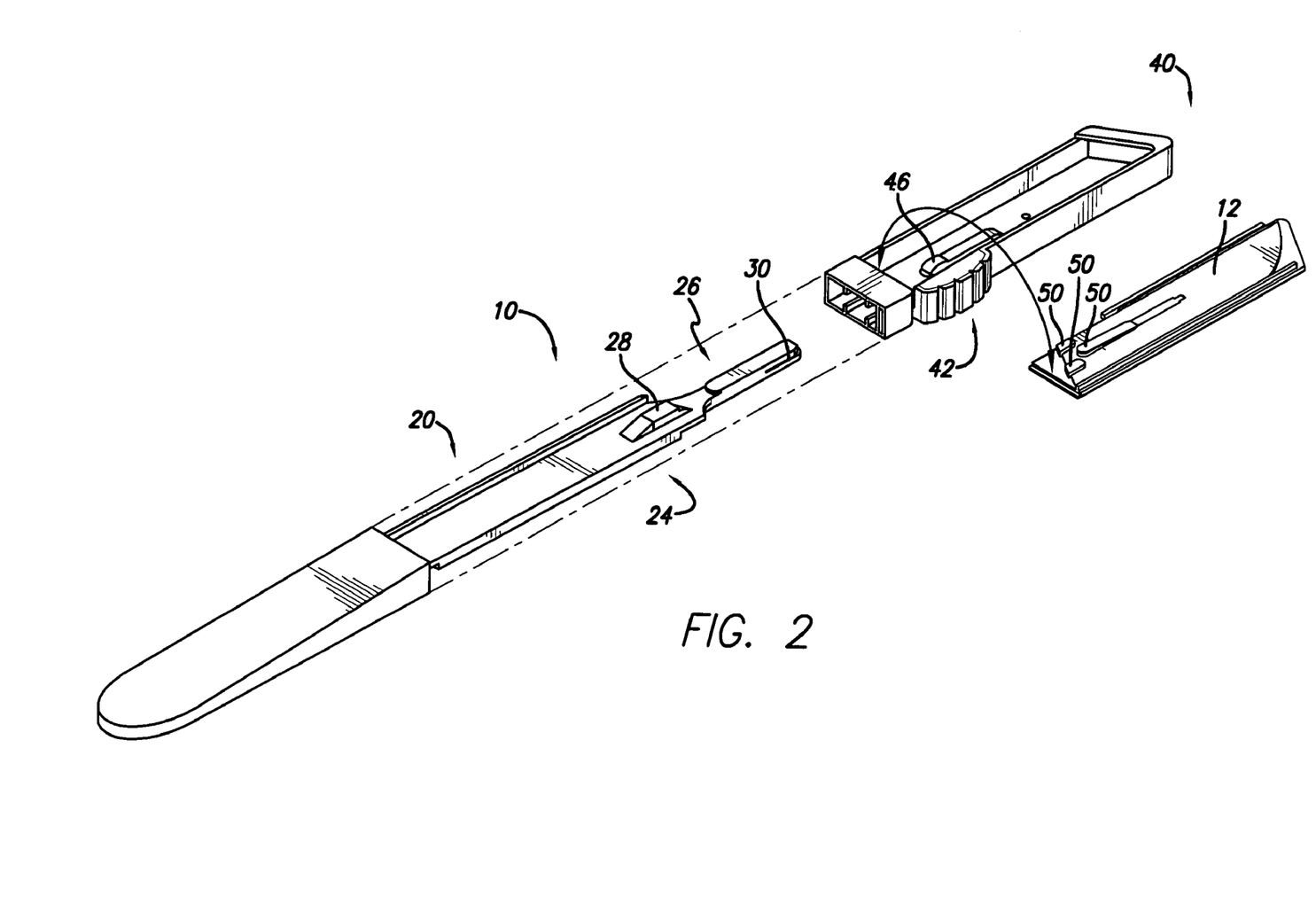
FIG. 2 is a perspective view of a safety scalpel system, showing the blade housing, according to an exemplary embodiment.

FIG. 2 shows a system 10, according to an exemplary embodiment, with housing 40 shown exploded. Housing 40 may include inner surfaces and outer surfaces. Housing 40 may further include one or more retaining members 50 that are configured to couple to and retain a blade 12 within housing. As shown, there are three retaining members, generally on the inner surfaces of housing 40. As shown there may be two retaining members 50, which may be configured to contact the non-cutting end of the blade 12, and one retaining member, which may be configured to enter the orifice 14 of blade 12. It will be appreciated that other shapes and configurations may be utilized for retaining members 50, as desired.

In this view, the interior portion of blade actuator 46 is shown in further detail. With this configuration, a blade 12 may be coupled to housing 40 by retaining members 50 and may be configured to slide onto blade receiving portion 26 and groove 30 to couple to handle 20. When it is desired that the blade be removed, blade actuator 46 may be actuated to bias blade 12 away from handle 20, and to recouple to retaining members 50 and housing 40.

Blade receiving portion 26 of handle 20 may further include a stop 28, which may be configured to contact the end of blade 12, such that blade 12 will securely fasten to handle when it is coupled to handle 20. This configuration may make the system more stable for use.

FIG. 3 shows an elevational view of system 10, again which may include handle 20, housing 40, and blade 12 (hidden). Blade 12 is retained in housing 40, and coupled to retaining members 50. As shown by the directional arrow, housing 40 may be moved toward handle 20, which again includes a blade receiving portion 26. In various embodiments, housing 40 may also include a tab or activator 42 and a stop member 44 which may be coupled to and/or integral with tab 42.

FIG. 4 shows housing 40 in the safety position, in which blade 12 is substantially, or completely enclosed by housing 40. Housing 40 may slide onto, or couple to, handle 20 and may remain in the safety position until tab or activator 42 is pressed in a generally downward direction and housing 40 is moved toward grasping structure 22 of handle 20. When housing 40 is in the safety position, it may completely enclose blade 12, except for an opening in the front of housing 40, to allow blade 12 to extend outwardly when housing 40 is in the blade exposed position. When tab or activator 42 is pressed in a generally downward direction stop member 44 engages top channel 32 such that it will slide within top channel 32 and allow housing 40 to move further toward grasping structure 22, as shown by the respective directional arrow.

As blade 12 is moved along channel 32, the blade receiving portion 26 may engage orifice 14 of blade 12. Also, when housing 40 is moved toward grasping structure 22, blade 12 may couple to blade receiving portion 26 and remain fixed with respect to handle 20

FIG. 4A shows a cross sectional view along line 4A—4A of FIG. 4. As shown, stabilizing members 48 may be configured to slide in, to couple to, top channel 32 and bottom channel 34 to allow housing 40 to slide onto handle 20.

FIG. 5 shows housing 40 in the blade exposed position where blade 12 is exposed for use by the user, and housing 40 is not covering blade 12 to allow the user to use blade 12. As shown by the directional arrows, when housing 40 is to be moved from the blade exposed position to the safety position, tab or activator 42 may be again pressed in a generally downward direction which would cause stop member 44 to engage top channel 32 to allow housing 40 to move away from grasping structure 22.

FIG. 6 again shows housing 40 in the safety position, enclosing blade 12. It will be appreciated that as shown by the directional arrows, tab or activator 42 may be pressed in a generally downward direction again to permit stop member 44 to engage top channel 32 and to allow housing 40 to be returned to the blade exposed position to allow re-use of blade 12 and housing 40, as shown in FIG. 7.

FIG. 7 again shows housing 40 in the blade exposed position, and again the directional arrows show the downward pressing of tab or activator 42 which allows stop member 44 to engage top channel 32 such that housing 40 may be moved again to the safety position, as shown in FIG. 8.

FIG. 8 shows housing 40 in the safety position. In this position, blade 12 may remain coupled to handle 20 via blade receiving portion 26 and groove 30 (not shown). Blade disengaging actuator 46 may then be actuated to disengage blade 12 from handle 20 and back to retaining members 50 (not shown), when housing 40 is moved in the direction of the directional arrow. Blade disengaging actuator 46 may contact blade 12 and bias blade 12 away from handle 12 and toward housing 40. In this manner blade 12 may selectively decouple and/or re-couple to and from housing 40 and handle 20 such that it may be removed safely and a new or different blade and/or housing and blade system may be utilized, as desired.

FIG. 9 again shows the housing 40 and the handle 20 separated after use such that the housing and blade may be safely removed and properly disposed of.

Figures 10, 11:
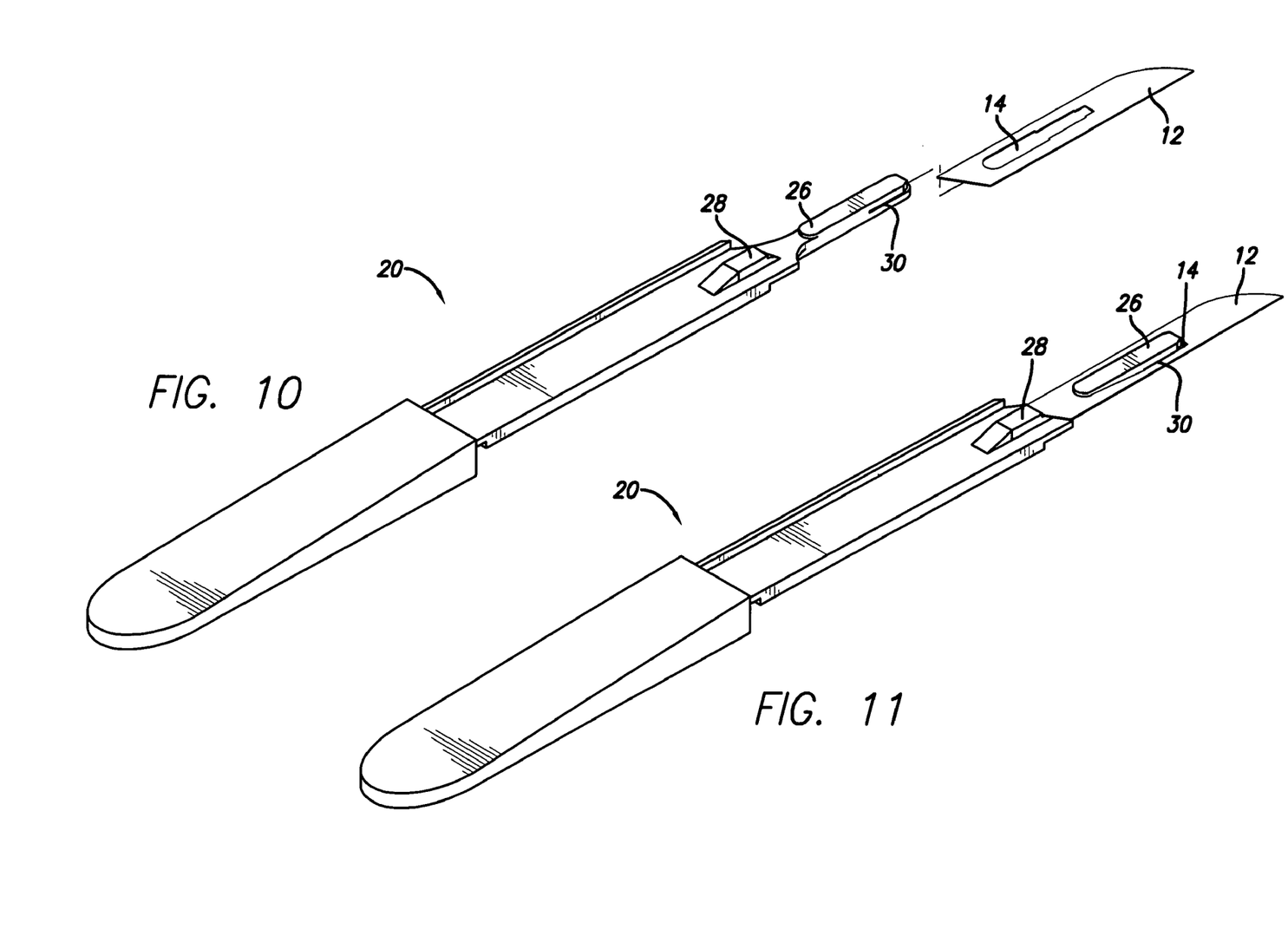
FIG. 10 is a perspective view of a handle and blade, according to an exemplary embodiment.
FIG. 11 is a perspective view of a handle and blade, according to an exemplary embodiment.

FIG. 10 shows a handle 20 and a blade 12 according to an exemplary embodiment. Blade 12 may include an orifice 14, as shown. Furthermore, handle 20 again may include a blade receiving portion 26 which may include a groove 30. Groove 30 may be configured to couple to blade 12 and orifice 14 such that the blade will slide onto groove 30 and encounter stop 28 as shown in FIG. 11. In this manner, bare blades may couple to handle 20 via this configuration. Furthermore, this may be generally the manner in which blade 12 couples to handle 20 when substantially being enclosed in housing 40 (not shown) when used within the system. Furthermore, handle 20 may be configured to receive bare blades and/or blades within safety housing 40. Yet further, handle 20 may be configured with weighting characteristics particular to each individual user, such that many may be made, and the user may be more comfortable with the weight and "feel" of handle 20.

Blade 12 may also be integral with handle 20, and housing 40 may move from a safety position to a blade exposed position. With this configuration the entire system may be disposable. Furthermore, blade 12 may also be made of plastic, and may be formed at, or near the same time as handle 20.

Handle 20 may be made from polymers, plastics, metals, rubber, and combinations thereof as desired. Blade 12 may be a typical scalpel blade such that it may be used alone with handle 20 and/or with the safety housing system 40. Blade 12 is typically a common scalpel blade. Many different types and styles of blades may be utilized with the handle 20 and the system 10. Housing 40 may be made in two parts as shown in FIG. 2, however other configurations may be utilized as desired, including made as a single injection molded piece. Housing may be made from plastics, polymers, rubber, metal, and combinations thereof, as desired.

Figure 12:
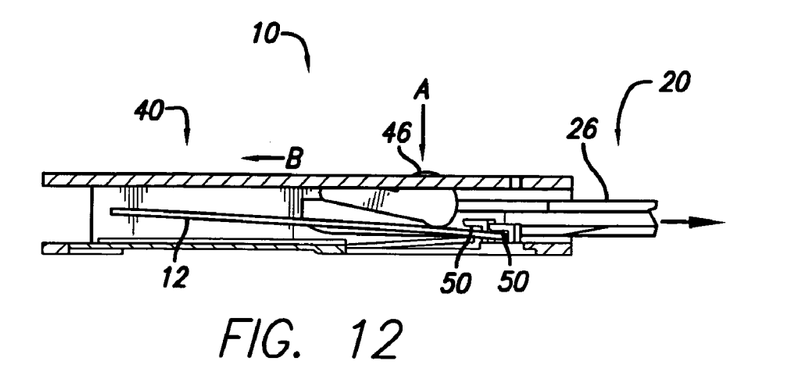
FIG. 12 is a top cross-sectional view of a blade housing and handle along line 12—12 from FIG. 8, according to an exemplary embodiment.

FIG. 12 shows a cross-sectional view of system 10 along lines 12—12 from FIG. 8. As shown, when blade disengaging actuator 46 is actuated downwardly as depicted by the directional arrow labeled A, it may contact blade 12 and disengage blade 12 from blade receiving portion 26 of handle 20 as housing 40 is moved in the direction of the directional arrow labeled B. Furthermore, when housing 40 is moved in the direction of the directional arrow B, away from handle 20, blade 12 will stay generally stationary with respect to housing 40 and may contact, and be coupled to, retaining members 50. In this manner, blade 12 may decouple from blade receiving portion 26 of handle 20 and selectively recouple to housing 40.

Figure 13:
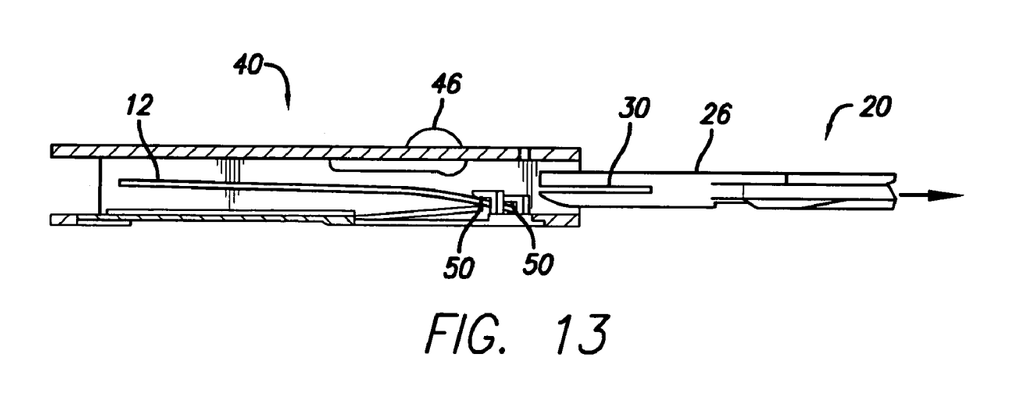
FIG. 13 is a top cross-sectional view of a blade housing disengaging a handle, according to an exemplary embodiment.

As shown in FIG. 13, handle 20 is removed from housing 40 while blade 12 stays generally stationary with respect to housing 40 and recouples to housing 40 via retaining members 50. Furthermore, blade actuator 46 returns to a steady state position as shown in FIG. 13. With this configuration, blades may easily selectively decouple from handle 20 and recouple to housing 40 such that the blade will not be exposed, which may increase the safety of users. Furthermore, housing and blade may then be disposed of, and/or put into a container to be counted later.

Housing 40 may selectively attach, detach, and reattach to handle 20, as desired. This configuration would allow a user to reuse a blade and housing, as needed.

It will be appreciated that many of the housing 40 and blade systems may be utilized and/or reutilized during one operation as the blades 12 become dull and/or if different blades are needed for different tasks. Furthermore, handles 20 may be utilized with or without a housing 40 and with a blade 12 separately such that in emergency situations a typical scalpel blade may be utilized without the housing 40 and blade system. Furthermore, handles 20 may be weighted, configured and/or designed to the particular preferences of the surgeon such that surgeons may be more likely to utilize them. Additionally, many handles 20 may be made to the specifications of a user, such that they may be thrown away and/or reused, as desired. With this configuration, handles may be more likely to be used by surgeons as they may conform to the surgeons' particular wants and needs as far as stiffness, weight, and other characteristics of a handle, among others.

In closing, it is to be understood that the exemplary embodiments described herein are meant to be merely illustrative of the general principles of the present invention. Other modifications that may be employed are within the scope of this disclosure. Thus, by way of example, but not of limitation, alternative configurations may be utilized in accordance with the teachings herein. Accordingly, the drawings and description are illustrative and not meant to be a limitation thereof. It is intended that the invention cover all embodiments and variations thereof as long as such embodiments and variations come within the scope of the appended claims and their equivalents.

What is claimed is:

1. A safety scalpel, comprising:
   a blade including an orifice disposed between a front cutting end and a rear end, said front and rear ends being disposed substantially in the same plane;
   a handle including a front portion and a rear portion, said front portion being adapted to receive said rear end of said blade and securely engage said blade via said orifice; and
   a housing configured to retain internally said blade and slide back and forth onto said front handle portion between a first position in which said front cutting end of said blade is fully exposed for operational use and a second position in which said front cutting end of said blade is fully enclosed within said housing for safety, said blade being securely engaged by said front handle portion via said orifice in said first and second positions, said housing including on different sides respectively a sliding movement activator and a blade disengaging actuator, said actuator configured for contacting to disengage said blade from said front handle portion when said housing is in said second position, said housing being formed with at least one retaining member unattached to said actuator, said retaining member forming a hooking structure for fixing therewithin a portion of said blade when said blade is disengaged from said handle and said blade disengaging actuator is disengaged from said blade;

said blade being removable with said housing from said handle.

2. The safety scalpel of claim 1, wherein said blade disengaging actuator is adapted to flex at a first end.

3. The safety scalpel of claim 2, wherein said blade disengaging actuator is adapted at a second end to push said internally retained blade toward said front handle portion when said blade housing is in said second position, said push causing said blade to disengage from said front handle portion, said second end being disposed substantially opposite said first flexing end.

4. The safety scalpel of claim 3, wherein said disengaged blade is retained internally by said housing for safety.

5. The safety scalpel of claim 4, wherein said housing is decoupled from said handle by sliding said housing away from said at least one groove on said front handle portion.

6. The safety scalpel of claim 5, wherein said blade is completely enclosed by said housing for safety when said housing is decoupled from said front handle portion.

7. The safety scalpel of claim 4, wherein said blade is retained internally by said housing via a plurality of integral blade retaining members.

8. The safety scalpel of claim 7, wherein said plurality of integral blade retaining members includes at least two members adapted to frictionally retain said rear end of said blade within said housing.

9. The safety scalpel of claim 7, wherein said plurality of integral blade retaining members includes at least one member adapted to engage said blade orifice within said housing.

10. The safety scalpel of claim 1, wherein said rear handle portion is adapted for hand grasping.

11. The safety scalpel of claim 1, wherein said front handle portion is equipped with at least one groove configured to fit into said blade orifice.

12. The safety scalpel of claim 11, wherein said front handle portion is further equipped with at least one guide channel, said at least one guide channel being flanked on one side by an integral locking bar.

13. The safety scalpel of claim 12, wherein said housing is adapted internally to slide within said at least one guide channel when activated.

14. The safety scalpel of claim 13, wherein said sliding movement activator includes a stop member at a first end, said stop member being adapted to lock said housing at opposite ends of said locking bar, said locked housing being respectively in one of said first and second positions.

15. The safety scalpel of claim 14, wherein said stop member is further adapted to unlock said housing and slide within said at least one guide channel when said sliding movement activator is pressed toward said locking bar in one of said first and second positions.

16. The safety scalpel of claim 14, wherein said sliding movement activator is adapted to flex at a second end, said second flexing end being disposed substantially opposite said stop member at said first end.

17. The safety scalpel of claim 1, wherein said retaining member retains said blade in deflected manner within said housing.

18. A safety scalpel, comprising:
a surgical blade;
a handle with a first portion adapted to engage said surgical blade, said first handle portion being equipped with at least one guide channel; and
a housing configured to retain internally said surgical blade, said housing including:
at least one interior stabilizing rail adapted to slide back and forth in said at least one guide channel of said first handle portion between a first position in which said surgical blade is exposed for operational use and a second position in which said surgical blade is fully enclosed within said housing for safety, said surgical blade being securely engaged by said first handle portion in said first and second positions;
a sliding movement activator;
a blade disengaging actuator configured to operate independently of said sliding movement activator for contacting to disengage said surgical blade from said handle, said sliding movement activator and said blade disengaging actuator being hinged respectively to adjacent sides of said housing; and,
at least one retaining member unattached to said actuator, said retaining member forming a hooking structure for fixing therewithin a portion of said blade when said blade is disengaged from said handle and said blade disengaging actuator is disengaged from said blade;
said surgical blade being removable with said housing from said handle.

19. The safety scalpel at claim 18, wherein said hinged actuator is configured to disengage said surgical blade from said first handle portion when said housing is in said second position.

20. The safety scalpel of claim 18, wherein said surgical blade includes:
a front cutting end;
a rear end; and
an orifice between said front and rear ends, said front and rear ends being disposed substantially in the same plane.

21. The safety scalpel of claim 18, wherein said surgical blade is completely enclosed by said housing for safety when said housing is decoupled from said first handle portion.

22. The safety scalpel of claim 18, wherein said retaining member retains said surgical blade in deflected manner within said housing.

23. A safety scalpel, comprising:
a blade;
a handle with a first portion adapted to engage said blade, said first handle portion including:
a locking bar; and
at least one guide channel being flanked on one side by said locking bar; and
a housing configured to retain internally said blade, said housing including:
at least one stabilizing rail adapted to slide back and forth in said at least one guide channel of said first handle portion between a first position in which said blade is exposed for operational use and a second position in which said blade is fully enclosed within said housing for safety, said blade being securely engaged by said first handle portion in said first and second positions;
a sliding movement activator adapted at one end to lock said housing at opposite ends of said locking bar to prevent surgical accidents, said locked housing being respectively in one of said first and second positions;
a blade disengaging actuator configured to operate independently of said sliding movement activator for contacting to disengage said blade from said handle, said sliding movement activator and said blade disengaging actuator being integrally formed respectively on different sides of said housing for operational safety; and, at least one retaining member unattached to said actuator, said retaining member forming a hooking structure for fixing therewithin a portion of said blade when said blade is disengaged from said handle and said blade disengaging actuator is disengaged from said blade;

said blade being removable with said housing from said handle.

24. The safety scalpel of claim 23, wherein said retaining member retains said blade in deflected manner within said housing.

25. A safety scalpel, comprising:

a blade;

a handle having a longitudinal axis and being adapted at one end to securely engage said blade, said handle including:

a locking bar being substantially parallel to said longitudinal axis; and at least one guide channel being flanked on one side by said locking bar; and a housing configured to retain internally said blade, said housing including:

at least one stabilizing rail adapted to slide back and forth in said at least one guide channel between a first position in which said blade is exposed for operational use and a second position in which said blade is fully enclosed within said housing for safety, said blade being securely engaged by said handle in said first and second positions;

a sliding movement activator integrally formed on a first side of said housing and adapted to lock said housing at opposite ends of said locking bar, said locked housing being respectively in one of said first and second positions;

an actuator integrally formed on a second side of said housing and configured for contacting to disengage said blade from said handle when said housing is in said second position, said first and second sides of said housing lying next to each other; and, at least one retaining member unattached to said actuator, said retaining member forming a hooking structure for fixing therewithin a portion of said blade when said blade is disengaged from said handle and said actuator is disengaged from said blade;

said blade being removable with said housing from said handle.

26. The safety scalpel of claim 25, wherein said retaining member retains said blade in deflected manner within said housing.

27. A safety scalpel, comprising:

a blade including a front cutting end, a substantially straight rear end, and an orifice operatively disposed between said front and rear ends;

a handle having a longitudinal axis and being adapted at one end to securely engage said blade via said orifice, said handle including:

a locking bar being substantially parallel to said longitudinal axis; and at least one guide channel being flanked on one side by said locking bar; and a housing configured to retain internally said blade, said housing including:

at least one stabilizing rail adapted to slide back and forth in said at least one guide channel between a first position in which said front cutting end of said blade is exposed for operational use and a second position in which said blade is frilly enclosed within said housing for safety, said substantially straight rear end of said blade being enclosed within said housing when said housing is in said first position;

a sliding movement activator integrally formed on a first side of said housing and adapted to lock said housing at opposite ends of said locking bar, said locked housing being respectively in one of said first and second positions;

an actuator integrally formed on a second side of said housing and configured for contacting to disengage said blade from said handle when said housing is in said second position, said first and second sides of said housing lying next to each other; and, at least one retaining member unattached to said actuator, said retaining member forming a hooking structure for fixing therewithin a portion of said blade when said blade is disengaged from said handle and said actuator is disengaged from said blade;

said blade being removable with said housing from said handle.

28. The safety scalpel of claim 27, wherein said retaining member retains said blade in deflected manner within said housing.

* * * * *